(12) United States Patent
Hashimoto et al.

(10) Patent No.: US 10,702,350 B2
(45) Date of Patent: Jul. 7, 2020

(54) ROBOT SYSTEM

(71) Applicant: KAWASAKI JUKOGYO KABUSHIKI KAISHA, Kobe-shi, Hyogo (JP)

(72) Inventors: Yasuhiko Hashimoto, Kobe (JP); Nobuyasu Shimomura, Kobe (JP); Tsuyoshi Maehara, Itami (JP); Masayuki Kamon, Akashi (JP); Yasushi Kurosawa, Kakogawa (JP); Shigetsugu Tanaka, Akashi (JP)

(73) Assignee: KAWASAKI JUKOGYO KABUSHIK KAISHA, Kobe-shi (JP)

( * ) Notice: Subject to any disclaimer, the term of this patent is extended or adjusted under 35 U.S.C. 154(b) by 273 days.

(21) Appl. No.: 15/755,304

(22) PCT Filed: May 27, 2016

(86) PCT No.: PCT/JP2016/002583
§ 371 (c)(1),
(2) Date: Feb. 26, 2018

(87) PCT Pub. No.: WO2017/033356
PCT Pub. Date: Mar. 2, 2017

(65) Prior Publication Data
US 2018/0243901 A1 Aug. 30, 2018

(30) Foreign Application Priority Data
Aug. 25, 2015 (JP) .................................. 2015-165479

(51) Int. Cl.
*G05B 19/418* (2006.01)
*A61B 34/37* (2016.01)
(Continued)

(52) U.S. Cl.
CPC .............. *A61B 34/37* (2016.02); *A61B 34/32* (2016.02); *B23P 19/04* (2013.01); *B23Q 15/12* (2013.01);
(Continued)

(58) Field of Classification Search
CPC ........ A61B 34/32; A61B 34/37; B23Q 15/12; Y10S 901/02; Y10S 901/03; Y10S 901/08; Y10S 901/09
See application file for complete search history.

(56) References Cited

U.S. PATENT DOCUMENTS 6,330,493 B1 * 12/2001 Takahashi et al.
2002/0029095 A1 * 3/2002 Kosaka et al.
(Continued)

FOREIGN PATENT DOCUMENTS

JP   S56-39884 A   4/1981
JP   S61-293787 A  12/1986
(Continued)

OTHER PUBLICATIONS

Jul. 26, 2016 International Search Report issued in International Patent Application No. PCT/JP2016/002583.

*Primary Examiner* — Harry Y Oh
(74) *Attorney, Agent, or Firm* — Oliff PLC

(57) ABSTRACT

A robot system includes a robot main body, memory part configured to store information for causing robot main body to perform given operation, as saved operational information, motion controller configured to control operation of robot main body by using saved operational information as automatic operational information for causing robot main body to operate, and an operation correcting device configured to generate, by being operated, manipulating information for correcting operation of robot main body during operation. Motion controller controls robot main body to (Continued)

perform an operation corrected from operation related to automatic operational information in response to a reception of the manipulating information while robot main body is operating by using automatic operational information. Memory part is configured to be storable of corrected operational information for causing robot main body to perform corrected operation as saved operational information, when robot main body performs corrected operation.

5 Claims, 5 Drawing Sheets

(51) Int. Cl.
| | |
|---|---|
| B23P 19/04 | (2006.01) |
| B25J 13/00 | (2006.01) |
| B25J 19/04 | (2006.01) |
| B25J 9/00 | (2006.01) |
| B25J 9/16 | (2006.01) |
| B25J 13/08 | (2006.01) |
| B25J 3/00 | (2006.01) |
| B25J 13/06 | (2006.01) |
| B25J 18/00 | (2006.01) |
| B25J 19/02 | (2006.01) |
| B25J 3/04 | (2006.01) |
| B23Q 15/12 | (2006.01) |
| B25J 13/02 | (2006.01) |
| B25J 11/00 | (2006.01) |
| G06F 3/01 | (2006.01) |
| H04N 5/232 | (2006.01) |
| H04N 7/18 | (2006.01) |
| A61B 34/32 | (2016.01) |
| G06T 7/62 | (2017.01) |
| G06T 7/70 | (2017.01) |
| B23P 21/00 | (2006.01) |

(52) U.S. Cl.
CPC . *B25J 3/00* (2013.01); *B25J 3/04* (2013.01); *B25J 9/0081* (2013.01); *B25J 9/0084* (2013.01); *B25J 9/161* (2013.01); *B25J 9/1602* (2013.01); *B25J 9/163* (2013.01); *B25J 9/1612* (2013.01); *B25J 9/1628* (2013.01); *B25J 9/1633* (2013.01); *B25J 9/1646* (2013.01); *B25J 9/1653* (2013.01); *B25J 9/1664* (2013.01); *B25J 9/1669* (2013.01); *B25J 9/1674* (2013.01); *B25J 9/1682* (2013.01); *B25J 9/1689* (2013.01); *B25J 9/1697* (2013.01); *B25J 11/008* (2013.01); *B25J 13/00* (2013.01); *B25J 13/003* (2013.01); *B25J 13/006* (2013.01); *B25J 13/02* (2013.01); *B25J 13/025* (2013.01); *B25J 13/06* (2013.01); *B25J 13/065* (2013.01); *B25J 13/08* (2013.01); *B25J 13/084* (2013.01); *B25J 13/085* (2013.01); *B25J 13/087* (2013.01); *B25J 13/088* (2013.01); *B25J 18/00* (2013.01); *B25J 19/023* (2013.01); *B25J 19/028* (2013.01); *B25J 19/04* (2013.01); *G05B 19/4182* (2013.01); *G06F 3/017* (2013.01); *G06T 7/62* (2017.01); *G06T 7/70* (2017.01); *H04N 5/23219* (2013.01); *H04N 7/181* (2013.01); *B23P 21/00* (2013.01); *B23P 21/002* (2013.01); *G05B 2219/33007* (2013.01); *G05B 2219/35464* (2013.01); *G05B 2219/37297* (2013.01); *G05B 2219/39004* (2013.01); *G05B 2219/39102* (2013.01); *G05B 2219/39439* (2013.01); *G05B 2219/39531* (2013.01); *G05B 2219/39533* (2013.01); *G05B 2219/40022* (2013.01); *G05B 2219/40134* (2013.01); *G05B 2219/40136* (2013.01); *G05B 2219/40139* (2013.01); *G05B 2219/40142* (2013.01); *G05B 2219/40143* (2013.01); *G05B 2219/40145* (2013.01); *G05B 2219/40146* (2013.01); *G05B 2219/40161* (2013.01); *G05B 2219/40162* (2013.01); *G05B 2219/40163* (2013.01); *G05B 2219/40169* (2013.01); *G05B 2219/40182* (2013.01); *G05B 2219/40183* (2013.01); *G05B 2219/40195* (2013.01); *G05B 2219/40387* (2013.01); *G05B 2219/40627* (2013.01); *Y10S 901/02* (2013.01); *Y10S 901/03* (2013.01); *Y10S 901/08* (2013.01); *Y10S 901/09* (2013.01); *Y10S 901/10* (2013.01); *Y10S 901/27* (2013.01); *Y10S 901/41* (2013.01); *Y10S 901/46* (2013.01); *Y10S 901/47* (2013.01)

(56) References Cited

U.S. PATENT DOCUMENTS

| | | | | |
|---|---|---|---|---|
| 2006/0287769 | A1* | 12/2006 | Yanagita | B25J 9/1669 |
| | | | | 700/245 |
| 2010/0268386 | A1* | 10/2010 | Kiyota | B25J 9/1674 |
| | | | | 700/264 |
| 2011/0015785 | A1* | 1/2011 | Tsusaka | B25J 9/0003 |
| | | | | 700/254 |
| 2011/0301733 | A1* | 12/2011 | Yoshima | B23K 9/0953 |
| | | | | 700/96 |
| 2012/0116585 | A1* | 5/2012 | Yoshima | B25J 9/1682 |
| | | | | 700/248 |
| 2012/0191245 | A1* | 7/2012 | Fudaba | B25J 3/04 |
| | | | | 700/254 |
| 2013/0310977 | A1* | 11/2013 | Tsusaka | B25J 9/163 |
| | | | | 700/257 |
| 2014/0172143 | A1* | 6/2014 | Fudaba | B25J 9/1656 |
| | | | | 700/108 |
| 2014/0379132 | A1* | 12/2014 | Fudaba | B25J 9/1689 |
| | | | | 700/260 |
| 2015/0148952 | A1* | 5/2015 | Shiratsuchi | B25J 9/0084 |
| | | | | 700/248 |
| 2016/0023355 | A1* | 1/2016 | Komatsu et al. | |
| 2018/0243916 | A1* | 8/2018 | Hashimoto | B25J 19/028 |

FOREIGN PATENT DOCUMENTS

| | | |
|---|---|---|
| JP | H01-124002 A | 5/1989 |
| JP | H05-245639 A | 9/1993 |
| JP | 2003-311661 A | 11/2003 |
| JP | 2006-244264 A | 9/2006 |
| JP | 2011-224696 A | 11/2011 |
| JP | 2011224696 * | 11/2011 |
| JP | 2013-071231 A | 4/2013 |

* cited by examiner

ROBOT SYSTEM

TECHNICAL FIELD

The present disclosure relates to a robot system.

BACKGROUND ART

Conventionally, an iterative work, such as welding, painting, assembling of components, and applicating of seal adhesive, is automatically performed in a manufacture site by an industrial robot. In order to make the robot to perform the work, the robot is necessary to be taught with information required for the work and store the information therein. A method of teaching the robot includes, for example, direct teaching by a teacher directly touching and moving the robot, teaching by a remote control using a teaching pendant, teaching by programming, and teaching by a master slave. For example, Patent Document 1 discloses one example of the teaching to store a route of a work to a robot arm by the direct teaching.

REFERENCE DOCUMENT OF CONVENTIONAL ART

[Patent Document]
[Patent Document 1] JP2013-071231A

DESCRIPTION OF THE DISCLOSURE

Problems to be Solved by the Disclosure

Meanwhile, part of the operation taught to the robot may be necessary to be changed from various reasons. For example, when an object to be worked, a work environment, etc. of the robot is partially changed from those when taught, problems, such as the robot becoming impossible to carry out the objective work, and the work accuracy becoming lowered, may arise. Moreover, after finishing the teaching, a fault may be discovered in the initially-created teaching information for part of the work. In such a case, the teaching information to be used for an automatic operation of the robot is changed by again performing the teaching. However, since an expert's skill is needed for the teaching in many cases, and many time and labors are required therefor, it is burdensome for the teacher. The same can be said for changing the part of robot operation.

Therefore, the purpose of the present disclosure is to provide a robot system, in which preset operation of a robot is easily correctable.

SUMMARY OF THE DISCLOSURE

In order to solve the above problem, a robot system according to one aspect of the present disclosure includes a robot main body, a memory part configured to store information for causing the robot main body to perform a given operation, as saved operational information, a motion controller configured to control the operation of the robot main body by using the saved operational information as automatic operational information for causing the robot main body to operate, and an operation correcting device configured to generate, by being operated, manipulating information for correcting the operation of the robot main body during operation. The motion controller controls the robot main body to perform an operation corrected from the operation related to the automatic operational information in response to a reception of the manipulating information while the robot main body is operating by using the automatic operational information. The memory part is configured to be storable of corrected operational information for causing the robot main body to perform the corrected operation as saved operational information, when the robot main body performs the corrected operation.

According to the above configuration, the operation of the robot main body during operation is correctable on real time by the operation correcting device. Thus, the partial correction of the operation of the robot main body can easily be performed. Moreover, since the corrected operational information for performing the corrected operation is stored in the memory part as the saved operational information, it is not necessary to make a correction by performing the same manipulation using the operation correcting device every time, but the corrected operation can be performed by the robot main body automatically. Therefore, preset operation of the robot is easily correctable.

In the robot system, the motion controller may control the operation of the robot main body using the latest saved operational information stored in the memory part as the automatic operational information. According to this configuration, the operation of the robot main body can gradually brought closer to the target operation each time the correction of the robot main body is repeated using the operation correcting device.

In the robot system, the memory part may store a plurality of saved operational information. The robot system may further include an operational information selector configured to be capable of selecting the saved operational information to be used as the automatic operational information, from the plurality of saved operational information stored in the memory part. According to this configuration, the robot main body can be operated by using the saved operational information stored when the correction is made more appropriately, as the automatic operational information.

In the robot system, the memory part may store a plurality of saved operational information. The robot system may further include a saved operational information generator configured to generate new saved operational information using the plurality of saved operational information stored in the memory part. According to this configuration, by using the plurality of saved operational information stored in the memory part, the saved operational information closer to the target operation can be generated.

In the robot system, the robot main body may be a slave arm, and the operation correcting device may be a master arm, for example, installed outside a workspace of the slave arm.

Effect of the Disclosure

The present disclosure is able to provide the robot system in which the preset operation of the robot is easily correctable.

MODES FOR CARRYING OUT THE DISCLOSURE

First Embodiment

Hereinafter, a robot system according to a first embodiment of the present disclosure is described with reference to the drawings. The robot system 100 according to this embodiment is a system using a master-slave type robot. In the robot system 100, the operator who is located at a position distant from a workspace of a slave arm 1 (outside of the workspace) manipulates a master arm 2 to input instructions so that the slave arm 1 is capable of performing operation corresponding to the instructions to perform a specific work. Moreover, in the robot system 100, the slave arm 1 is also capable of automatically performing a given work, without the operator's manipulation of the master arm 2.

An operating mode in which the slave arm 1 is operated according to the instruction inputted through the master arm 2 is herein referred to as a "manual mode." Note that the "manual mode" described above also includes a case where part of the operation of the slave arm 1 under operation is automatically corrected based on the instruction inputted by the operator manipulating the master arm 2. Moreover, an operating mode in which the slave arm 1 is operated according to a preset task program is referred to as an "automatic mode."

Further, in the robot system 100 of this embodiment, it is configured so that the operation to be carried out automatically is correctable by reflecting the manipulation of the master arm 2 on the automatic operation of the slave arm 1, while the slave arm 1 is operating automatically. An operating mode in which the slave arm 1 is operated according to the preset task program, while an instruction inputted through the master arm 2 is reflectable is herein referred to as a "correctable automatic mode." Note that the "automatic mode" described above is distinguished from the "correctable automatic mode" in that the manipulation of the master arm 2 is not reflected on the operation of the slave arm 1 when the operating mode in which the slave arm 1 is operated is the automatic mode.

Figure 1:
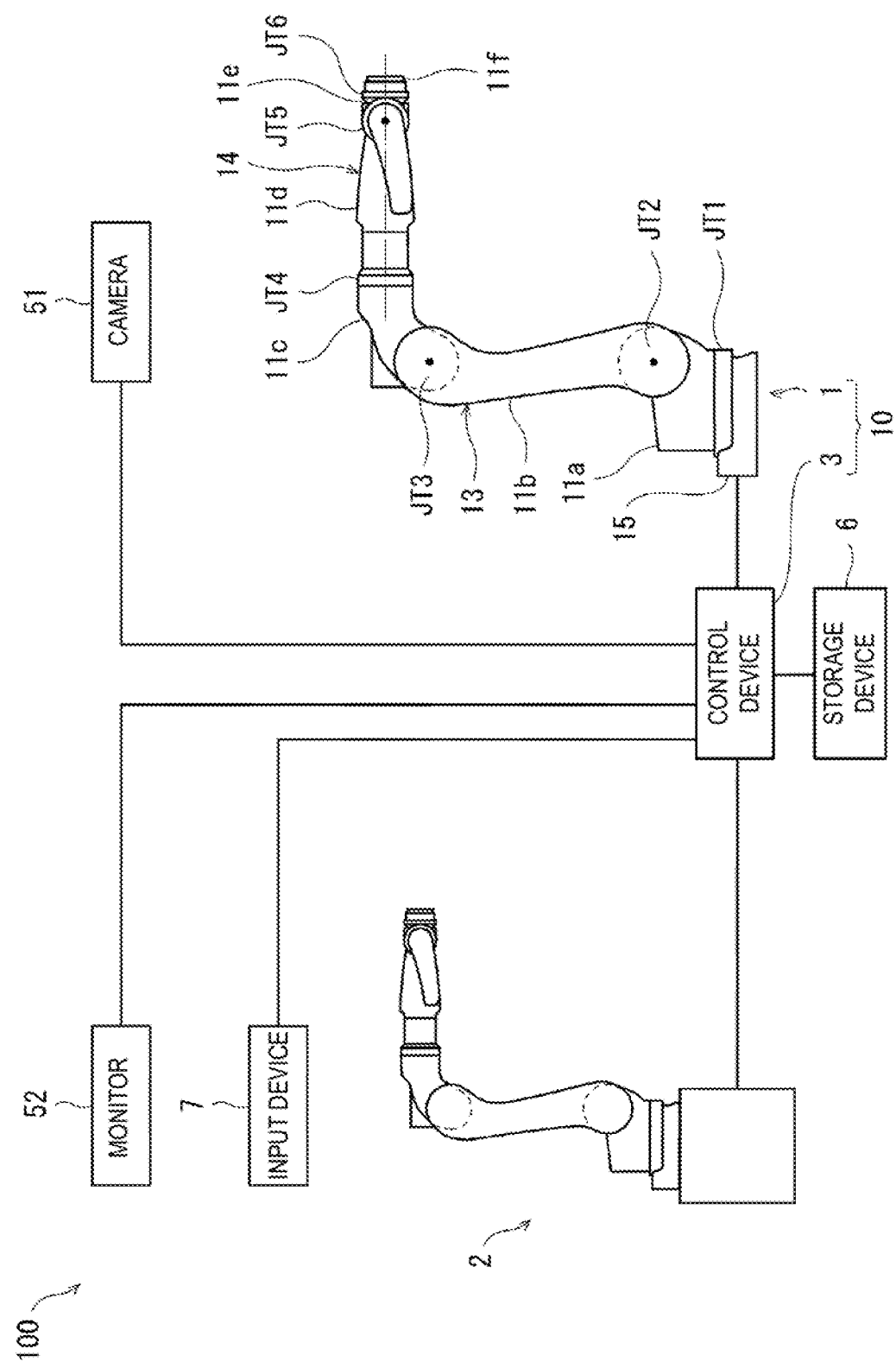
FIG. 1 is a schematic view illustrating a configuration of a robot system according to a first embodiment.

First, with reference to FIG. 1, a configuration of the robot system 100 according to this embodiment is described. FIG. 1 is a schematic view illustrating one example of the configuration of the robot system 100 according to this embodiment. As illustrated in FIG. 1, the robot system 100 is comprised of a slave robot 10, a master arm 2, a camera 51, a monitor 52, a storage device 6, and an input device 7. Below, each component of the robot system 100 is described in detail.

(Configuration of Slave Robot 10)

The slave robot 10 includes a slave arm 1, an end effector (not illustrated) attached to a tip end of the slave arm 1, and a control device 3 which governs the operations of the slave arm 1 and the end effector. The slave arm 1 includes a pedestal 15, an arm part 13 supported by the pedestal 15, and a wrist part 14, which is supported by a tip end of the arm part 13 and to which the end effector is attached.

As illustrated in FIG. 1, the slave arm 1 is an articulated robot arm having a plurality (three or more) joints JT1-JT6, and is constructed by serially connecting a plurality of links 11a-11f. In more detail, at the first joint JT1, the pedestal 15 and a base-end part of the first link 11a are coupled to each other so as to be rotatable about an axis extending vertically. At the second joint JT2, a tip-end part of the first link 11a and a base-end part of the second link 11b are coupled to each other so as to be rotatable about an axis extending horizontally. At the third joint JT3, a tip-end part of the second link 11b and a base-end part of the third link 11c are coupled to each other so as to be rotatable about an axis extending horizontally. At the fourth joint JT4, a tip-end part of the third link 11c and a base-end part of the fourth link 11d are coupled to each other so as to be rotatable about an axis extending in the longitudinal directions of the fourth link 11c. At the fifth joint JT5, a tip-end part of the fourth link 11d and a base-end part of the fifth link 11e are coupled to each other so as to be rotatable about an axis perpendicular to the longitudinal directions of the link 11d. At the sixth joint JT6, a tip-end part of the fifth link 11e and a base-end part of the sixth link 11f are twistably and rotatably coupled to each other. A mechanical interface is provided to a tip-end part of the sixth link 11f. The end effector corresponding to the contents of work is attached to the mechanical interface so as to be attachable and detachable.

The arm part 13 of the slave arm 1 is formed with a coupled body of links and joints comprised of the first joint JT1, the first link 11a, the second joint JT2, the second link 11b, the third joint JT3, and the third link 11c, described above. Moreover, the wrist part 14 of the slave arm 1 is formed with a coupled body of links and joints comprised of the fourth joint JT4, the fourth link 11d, the fifth joint JT5, the fifth link 11e, the sixth joint JT6, and the fourth link 11f, described above.

The joints JT1-JT6 are provided with drive motors M1-M6, respectively, as one example of an actuator which relatively rotates two members coupled by each joint. The drive motors M1-M6 are, for example, servo motors which are servo-controlled by the control device 3. Moreover, the joints JT1-JT6 are provided with rotation sensors E1-E6 (see FIG. 3) for detecting rotation positions of the drive motors M1-M6, and current sensors C1-C6 (see FIG. 3) for detecting current which controls the rotation of the drive motors M1-M6, respectively. The rotation sensors E1-E6 are, for example, encoders. Note that the description of the drive motors M1-M6, the rotation sensors E1-E6, and the current sensors C1-C6 described above are denoted by attaching the suffix of 1-6 to the alphabet corresponding to each of the joints JT1-JT6. Below, when arbitrary joint is illustrated among the joints JT1-JT6, the joint is referred to as "JT" while omitting the suffix, and the same is applied to the drive motor M, the rotation sensor E, and the current sensor C.

The control device 3 may be comprised of, for example, an arithmetic part (not illustrated), such as a microcontroller, a MPU and a PLC (Programmable Logic Controller), and a logic circuit, and a memory part (not illustrated), such as a ROM, and a RAM.

Figure 2:
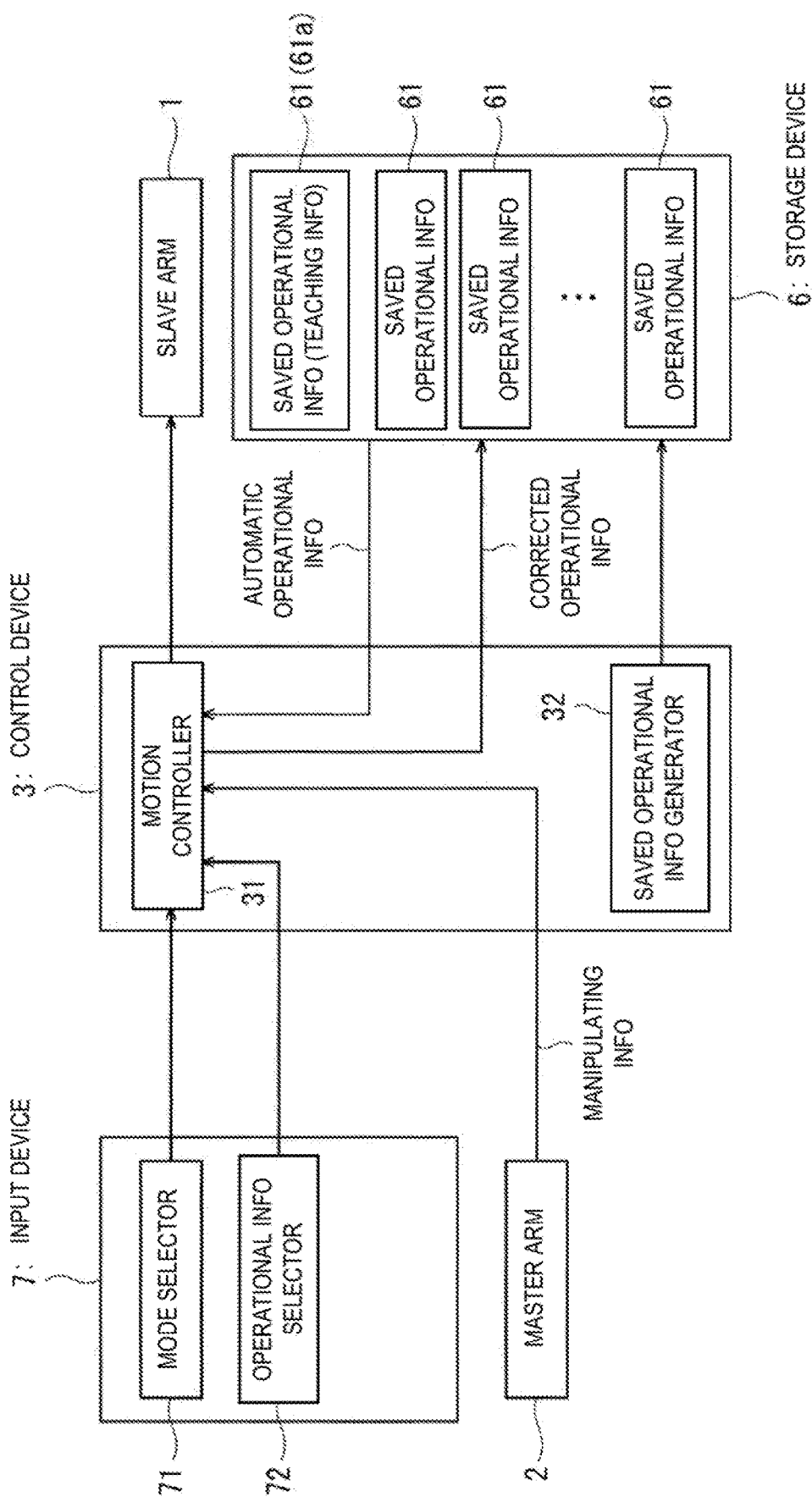
FIG. 2 is a schematic view illustrating a configuration of a control system of the robot system illustrated in FIG. 1.

FIG. 2 is a schematic view illustrating a configuration of a control system of the robot system 100. As illustrated in FIG. 2, the control device 3 is provided with a motion controller 31 as a functional block. The motion controller 31 controls the operation of the slave arm 1. Control of the operation of the slave arm 1 by the motion controller 31 is described later in detail. The functional block provided to the control device 3 is implemented by, for example, the arithmetic part of the control device 3 reading and executing the program stored in the memory part.

(Configuration of Master Arm 2)

The master arm 2 is a device which is installed outside the workspace of the slave arm 1 and receives an operating instruction from the operator. Since the master arm 2 has a similarity structure to the slave arm 1, description of the configuration of the master arm 2 is omitted. Note that the master arm 2 may have a non-similarity structure to the slave arm 1. Manipulating information is generated by manipulating the master arm 2, and the generated manipulating information is sent to the control device 3. In the robot system 100 of this embodiment, the slave arm 1 is controlled by the control device 3 so that it moves so as to follow the motion of the master arm 2, when the manipulating information is sent to the control device 3 while the operating mode in which the slave arm 1 is operated is the manual mode. When the manipulating information is sent to the control device 3 while the operating mode in which the slave arm 1 is operated is the correctable automatic mode, the operation of the slave arm 1 which operates automatically is corrected using the manipulating information. In this embodiment, the master arm 2 functions as an operation correcting device which corrects the operation of the slave arm 1 during operation, as will be described later.

(Camera 51 and Monitor 52)

Returning to FIG. 1, the camera 51 is a camera which images a work situation of the slave arm 1, and the monitor 52 is a monitor by which the operator checks the work situation of the slave arm 1. The camera 51 is installed in a space where the slave arm 1 is provided, and the monitor 52 is installed in a space where the master arm 2 is provided. The operator manipulates the master arm 2, while looking at the work situation of the slave arm 1 displayed on the monitor 52. The camera 51 and the monitor 52 are connected with each other through the control device 3, and image information imaged by the camera 51 is sent to the monitor 52 through the control device 3. Note that the camera 51 and the monitor 52 may be directly connected to each other without having the control device 3 therebetween, or may be connected with each other through another device. The camera 51 and the monitor 52 may be connected with each other wiredly or wirelessly.

(Input Device 7)

The input device 7 is an input device which is installed outside the workspace together with the master arm 2, receives the operating instruction from the operator, and inputs the received operating instruction into the control device 3. The input device 7 is operably configured, and may include, for example, a switch, an adjustment knob, a control lever, or a mobile terminal, such as a tablet computer.

As illustrated in FIG. 2, the input device 7 includes a mode selector 71 and an operational information selector 72. The mode selector 71 is to allow the operator to select the operating mode in which the slave arm 1 is operated from the automatic mode, the correctable automatic mode, and the manual mode, which are described above. The operational information selector 72 is to select operational information from a plurality of operational information for operating the slave arm 1, which is used by the motion controller 31 when operating the slave arm 1 in the automatic mode or the correctable automatic mode.

(Storage Device 6)

The storage device 6 is a readable and writable recording medium, and stores information for causing the slave arm 1 to automatically perform a given operation, as saved operational information 61. The saved operational information 61 needs not to be all information necessary to cause the slave arm 1 to automatically perform the given operation, but may be part of the information. Moreover the saved operational information 61 may be any kind of information, as long as it is information related to the operation of the slave arm 1. For example, the saved operational information 61 may be route information containing time-series data, or may be path information indicative of a pause of discontinuous points. The saved operational information 61 may also contain, for example, a speed of the slave arm 1 along the route.

The storage device 6 stores at least one saved operational information 61, and one of them is, for example, teaching information 61a which is stored by operating the slave arm 1 so as to perform the given work by teaching. In this embodiment, although the saved operational information 61 as the teaching information 61a is information stored by manipulating the master arm 2 to instruct the operation of the slave arm 1, it is not limited to this configuration but may be information stored in any teaching method. For example, the saved operational information 61 as the teaching information 61a may be information stored by direct teaching. Note that, in the robot system 100 according to this embodiment, although the storage device 6 is provided separately from the control device 3 but may be provided integrally with the control device 3.

Below, the control of the operation of the slave arm 1 by the motion controller 31 is described with reference to FIG. 2.

One of the at least one saved operational information 61 stored in the storage device 6 is sent to the motion controller 31 as automatic operational information for causing the slave arm 1 to automatically operate. In addition, the manipulating information generated by manipulating the master arm 2 is sent to the motion controller 31.

The motion controller 31 uses one or both of the automatic operational information and the manipulating information according to the operating mode selected in the mode selector 71.

When the operating mode selected in the mode selector 71 is the manual mode, the motion controller 31 uses the manipulating information. In more detail, when the operating mode in which the slave arm 1 is operated is the manual mode, the motion controller 31 controls the operation of the slave arm 1 according to the manipulating information (inputted instruction) sent by manipulating the master arm 2, without using the saved operational information 61 in the storage device 6.

Moreover, when the operating mode selected in the mode selector 71 is the automatic mode, the motion controller 31 uses the automatic operational information. In more detail, when the operating mode in which the slave arm 1 is operated is the automatic mode, the motion controller 31 controls the operation of the slave arm 1 using the automatic operational information sent from the storage device 6 according to the preset task program, without using the manipulating information sent from the master arm 2.

Moreover, when the operating mode selected in the mode selector 71 is the correctable automatic mode, the motion controller 31 uses both the automatic operational information and the manipulating information. Note that, when the operating mode is the correctable automatic mode and the manipulating information is not sent to the motion controller 31, the motion controller 31 uses only the automatic operational information. In more detail, when the operating mode in which the slave arm 1 is operated is the correctable automatic mode, and the manipulating information is received while the slave arm 1 is operating automatically using the automatic operational information, the motion controller 31 controls the operation of the slave arm 1 by using both the automatic operational information and the manipulating information. Thus, the slave arm 1 performs operation corrected from the operation related to the automatic operational information, i.e., the operation to be performed automatically.

Figure 3:
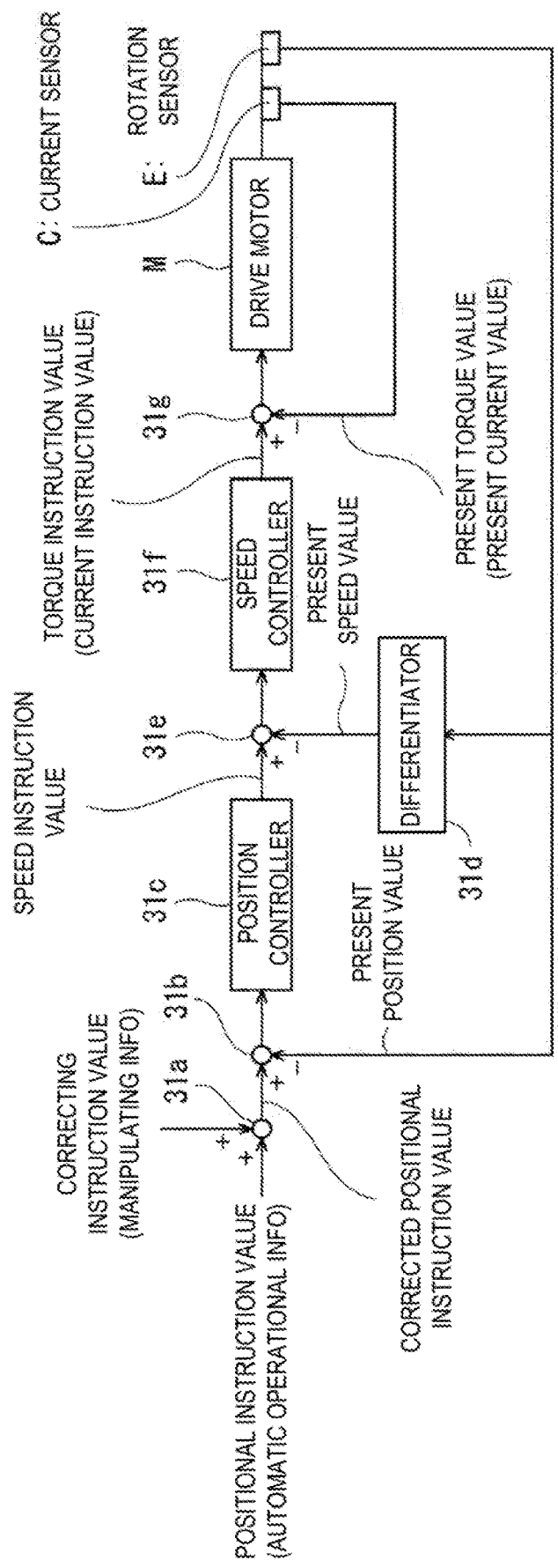
FIG. 3 is a view illustrating one example of a block diagram of a control system of a motion controller illustrated in FIG. 2.

Below, the correction of the operation of the slave arm 1 when the operating mode in which the slave arm 1 is operated is the correctable automatic mode is described with reference to FIG. 3. FIG. 3 is a view illustrating one example of a block diagram of a control system of the motion controller 31. In this example, the automatic operational information and the manipulating information are route information which contains, for example, time-series data.

The motion controller 31 includes an adder 31a, subtractors 31b, 31e and 31g, a position controller 31c, a differentiator 31d, and a speed controller 31f, and controls the rotation position of the drive motor M of the slave arm 1 according to an instruction value based on the automatic operational information and an instruction value based on the manipulating information.

The adder 31a generates a corrected positional instruction value by adding a correcting instruction value based on the manipulating information to a positional instruction value based on the automatic operational information. The adder 31a sends the corrected positional instruction value to the subtractor 31b.

The subtractor 31b subtracts a present position value detected by the rotation sensor E from the corrected positional instruction value to generate an angular deviation. The subtractor 31b sends the generated angular deviation to the position controller 31c.

The position controller 31c generates a speed instruction value based on the angular deviation sent from the subtractor 31b by calculation processing based on a predefined transfer function and/or a predefined proportionality coefficient. The position controller 31c sends the generated speed instruction value to the subtractor 31e.

The differentiator 31d differentiates the present position value information detected by the rotation sensor E, and generates an amount of change in the rotation angle of the drive motor M per unit time, i.e., a present speed value. The differentiator 31d sends the generated present speed value to the subtractor 31e.

The subtractor 31e subtracts the present speed value sent from the differentiator 31d from the speed instruction value sent from the position controller 31c to generate a speed deviation. The subtractor 31e sends the generated speed deviation to speed controller 31f.

The speed controller 31f generates a torque instruction value (current instruction value) based on the speed deviation sent from the subtractor 31e by calculation processing based on a predefined transfer function and/or a predefined proportionality coefficient. The speed controller 31f sends the generated torque instruction value to the subtractor 31g.

The subtractor 31g subtracts a present current value detected by the current sensor C from the torque instruction value sent from the speed controller 31f to generate a current deviation. The subtractor 31g sends the generated current deviation to the drive motor M to drive the drive motor M.

Thus, the motion controller 31 controls the drive motor M to control the slave arm 1 so that the slave arm 1 performs the operation corrected from the operation related to the automatic operational information. Note that, when the operating mode of the slave arm 11 is the automatic mode, the positional instruction value based on the automatic operational information is sent to the subtractor 31b, and when the operating mode of the slave arm 11 is the manual mode, the positional instruction value based on the manipulating information is sent to the subtractor 31b.

The storage device 6 is configured, when the slave arm 1 performs the corrected operation, to automatically store corrected operational information for the slave arm 1 to perform the corrected operation as the saved operational information 61. Note that the storage device 6 may be configured, when the slave arm 1 performs the corrected operation, to be selectable of whether the corrected operational information described above is to be stored as the saved operational information 61. In this case, for example, after the corrected operation of the slave arm 1 is finished, the control device 3 may be configured to inquire the input device 7 of whether the corrected operation is to be stored.

The motion controller 31 can use the corrected operational information stored in the storage device 6 as the saved operational information 61 as the automatic operational information in operation on and after next time. In this embodiment, the motion controller 31 is configured to control the operation of the slave arm 1 using the latest saved operational information 61 stored in the storage device 6 as the automatic operational information.

Figure 4:
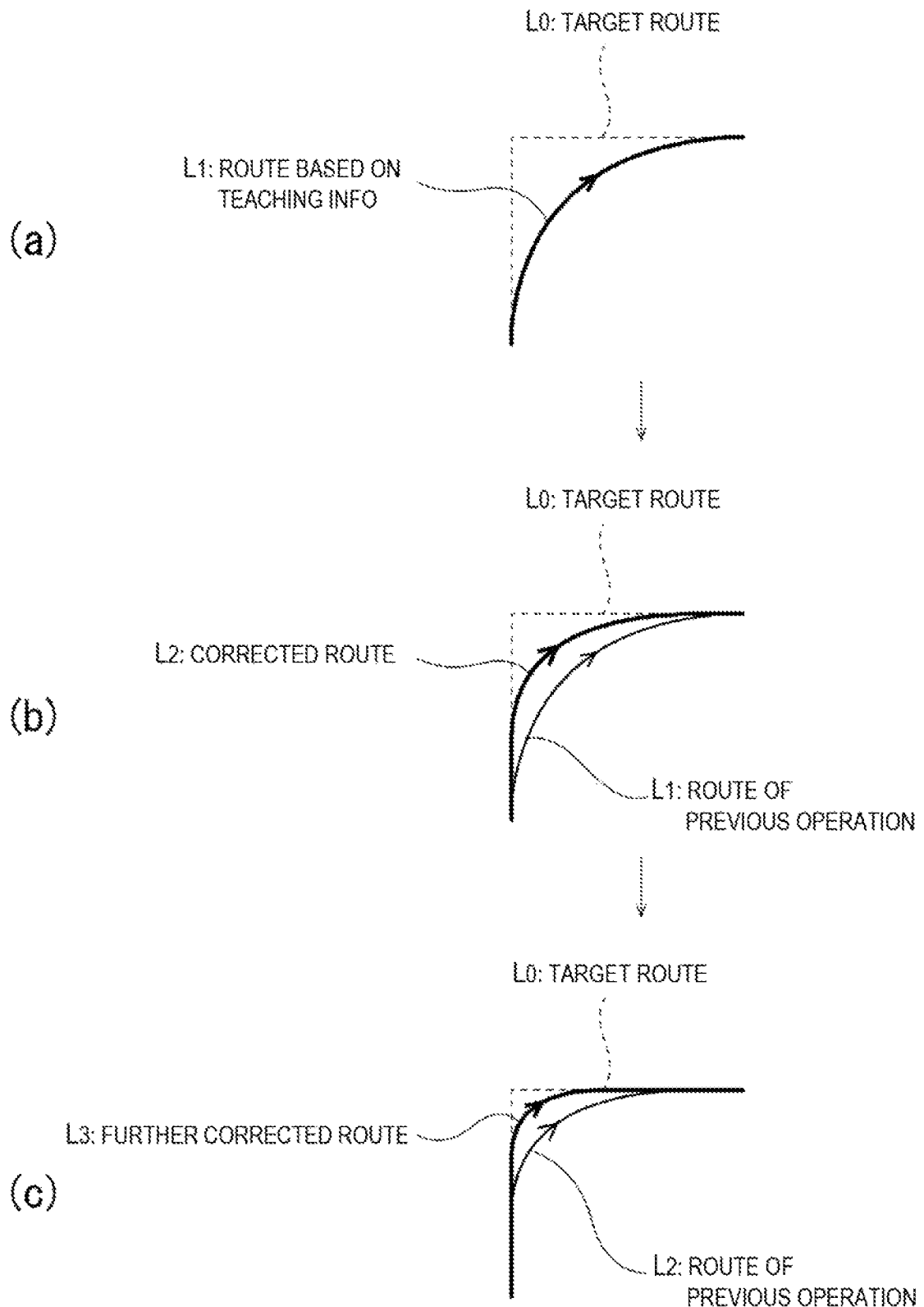
FIG. 4 is a view illustrating one example of correction of robot operation by the robot system illustrated in FIG. 1.

Below, with reference to FIGS. 4(a) to (c), the operation correction of the slave arm 1 by the robot system 100 is described, while one example thereof is given. FIGS. 4(a) to (c) illustrate that, when the operating mode in which the slave arm 1 is operated is the correctable automatic mode, a route of the slave arm 1 (i.e., a route of the end effector) is corrected to a target route $L_0$ each time the slave arm 1 is operated. FIGS. 4(a) to (c) illustrate the target route $L_0$ having a right-angled corner by a dashed line.

In FIG. 4(a), a route $L_1$ of the slave arm 1 when operating the slave arm 1 using the teaching information 61a as the automatic operational information without the manipulation of the master arm 2 is illustrated by a thick line. It can be seen from FIG. 1 that the actual route $L_1$ is partially deviated from the target route $L_0$ (especially, at the corner of the route $L_0$).

In FIG. 4(b), a route $L_2$ of the slave arm 1 when manipulating the master arm 2 so that an amount of deviation from the target route $L_0$ becomes smaller than the route $L_1$ at the time of the previous operation (the route of FIG. 4(a)) is illustrated by a thick line. Note that, in FIG. 4(b), the route $L_1$ of the previous operation is illustrated by a thin line for reference.

The operator manipulates the master arm 2 so that the amount of deviation from the target route $L_0$ becomes smaller than the route $L_1$ at the time of the previous operation, to correct the operation of the slave arm 1 to the route $L_2$ which is corrected from the route $L_1$. Specifically, the motion controller 31 operates the slave arm 1 using the teaching information 61a as the automatic operational information in the state where the correctable automatic mode is selected as the operating mode in which the slave arm 1 is operated. The operator manipulates the master arm 2 while the slave arm 1 is operating using the automatic operational information, so that the route approaches the target route $L_0$ from the previous route $L_1$. Thus, the route is corrected to the route $L_2$ of the slave arm 1 from the route $L_1$ of the slave arm 1. The corrected operational information for operating the slave arm 1 so that the slave arm 1 traces the route $L_2$ is stored in the storage device 6 as the saved operational information 61.

In this embodiment, the motion controller 31 is configured to control the operation of the slave arm 1 using the latest saved operational information 61 stored in the storage device 6 as the automatic operational information. Thus, when the master arm 2 is not manipulated in a subsequent operation, the slave arm 1 operates so as to trace the route $L_2$.

In FIG. 4(c), a route $L_3$ of the slave arm 1 when manipulating the master arm 2 so that the amount of deviation from the target route $L_0$ becomes smaller than the route $L_2$ at the time of the previous operation (route of FIG. 4(b)) is illustrated by a thick line. Note that, in FIG. 4(c), the route $L_2$ of the previous operation is illustrated by a thin line for reference.

The operator manipulates the master arm 2 so that the amount of deviation from the target route $L_0$ becomes smaller than the route $L_2$ at the time of the previous operation to correct the operation of the slave arm 1 to the route $L_3$ which is corrected from the route $L_2$. Specifically, the motion controller 31 operates the slave arm 1 using the saved operational information 61 related to the route $L_2$ as the automatic operational information, while the correctable automatic mode is selected as the operating mode in which the slave arm 1 is operated. The operator manipulates the master arm 2 so that the route approaches the target route $L_0$ from the previous route $L_2$ while the slave arm 1 is operating using the automatic operational information. Thus, the route is corrected to the route $L_3$ of the slave arm 1 from the route $L_2$ of the slave arm 1. The corrected operational information for operating the slave arm 1 so that the slave arm 1 traces the route $L_3$ is stored in the storage device 6 as the saved operational information 61.

Thus, the route of the slave arm 1 is corrected so as to approach the target route $L_0$ each time the slave arm 1 is operated. When the route of the slave arm 1 is corrected to the target route $L_0$ and a further correction becomes unnecessary, the operator selects the automatic mode with the mode selector 71 as the operating mode in which the slave arm 1 is operated, to operate the slave arm 1 in the completely automatic fashion.

As described above, in the robot system 100 according to this embodiment, the operation of the slave arm 1 during operation is correctable on real time by the master arm 2 which functions as the operation correcting device. Thus, the partial correction of the operation of the slave arm 1 can easily be performed. Moreover, since the corrected operational information for performing the corrected operation is stored in the storage device 6 as the saved operational information, it is not necessary to make a correction by performing the same manipulation using the master arm 2 every time, but the corrected operation can be performed by the slave arm 1 automatically.

Therefore, the operation taught to the slave arm 1 is easily correctable.

Moreover, in this embodiment, since the automatic mode is selectable as the operating mode of the motion controller 31 by the mode selector 71, the automatic mode is selected when the correction of the operation of the slave arm 1 is not necessary to prevent that the master arm 2 which is the operation correcting device is unintentionally operated and the operation of the slave arm 1 is corrected. Moreover, since the manual mode is selectable as the operating mode of the motion controller 31 by the mode selector 71, the slave arm 1 is operable without using the saved operational information 61 stored in the storage device 6.

Moreover, in this embodiment, since the motion controller 31 controls the operation of the slave arm 1 using the latest saved operational information stored in the storage device 6 as the automatic operational information, the operation of the slave arm 1 can be gradually brought closer to the target operation each time the correction of the slave arm 1 is repeated using the master arm 2.

The motion controller 31 is not necessary to use the latest saved operational information 61 stored in the storage device 6 as the automatic operational information. For example, the operational information selector 72 may select the saved operational information 61 from a plurality of saved operational information 61 stored in the storage device 6, which is to be used by the motion controller 31 as the automatic operational information. In this case, the same saved operational information 61 may be used every time as the automatic operational information until the operational information selector 72 selects the saved operational information 61 to be used as the automatic operational information. According to this configuration, even when the latest saved operational information 61 stored in the storage device 6 is not the optimal as information for operating the slave arm 1, the operational information selector 72 is capable of using the saved operational information 61 when the correction is made appropriately, as the automatic operational information.

Moreover, the robot system 100 may be provided with a situation information acquiring part (not illustrated) which acquires situation information indicative of the situation of the slave arm 1 in the workspace, and the motion controller 31 may select the saved operational information 61 suitable for operating the slave arm 1 as the automatic operational information, based on the situation information acquired by the situation information acquiring part. The situation information includes, for example, information used for recognizing the position or posture of the slave arm 1 in the workspace, or the situation around the slave arm 1. The information used for recognizing the situation around the slave arm 1 is, for example, a time window or timing at which the slave arm 1 is operated, or temperature and/or humidity in the workspace. For example, if the slave robot 10 is a sealing robot which applies seal adhesive with viscosity, the viscous resistance of the seal adhesive may vary depending on the time of work. In such a case, by selecting the saved operational information 61 suitable for the viscous resistance of the seal adhesive as the automatic operational information based on the situation information, the correction of the operation of the slave arm 1 can also be made more easily.

Moreover, as illustrated in FIG. 2, the motion controller 31 may be provided with a saved operational information generator 32 which generates new saved operational information 61 using a plurality of saved operational information 61 stored in the storage device 6. A method of generating the new saved operational information 61 by the saved operational information generator 32 is not limited in particular, but an algorithm suitable for bringing the operation closer to the target operation is adopted. For example, the saved operational information generator 32 may be configured to generate the saved operational information 61 for performing operation which is an average of the operations related to the plurality of saved operational information which is stored. The saved operational information generator 32 may delete the saved operational information 61 on the past used in order to generate the new saved operational information 61, when generating the new saved operational information 61.

Moreover, in this embodiment, although the master arm 2 which is manipulatable of the route of the end effector of the slave arm 1 is described as the operation correcting device of the present disclosure, it may be, for example, a route manipulating device having another configuration, such as a joystick.

Second Embodiment

Figure 5:
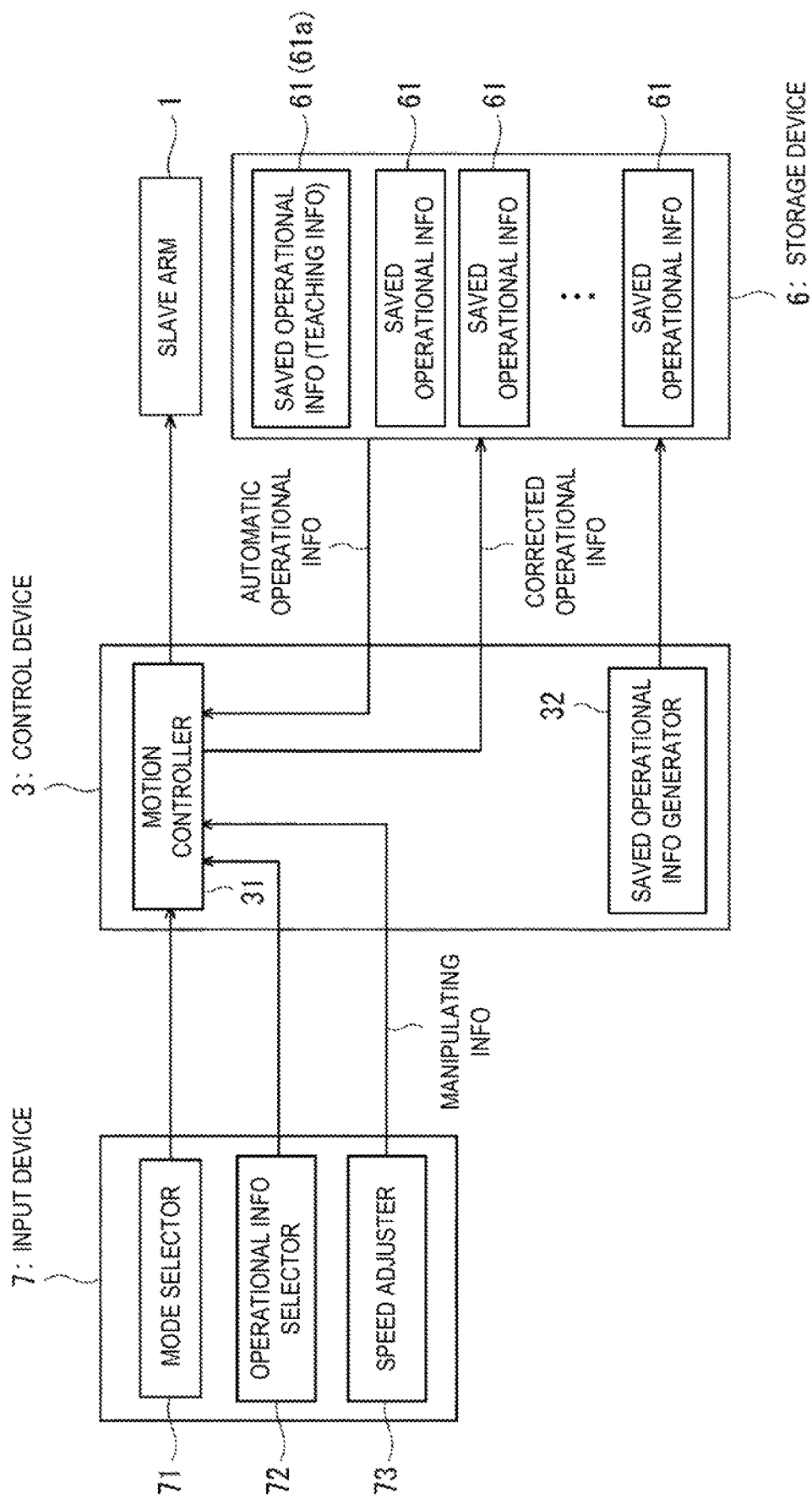
FIG. 5 is a schematic view illustrating a configuration of a control system of a robot system according to a second embodiment.

Next, with reference to FIG. 5, a robot system according to a second embodiment is described. FIG. 5 is a schematic view illustrating a configuration of a control system of the robot system according to the second embodiment.

In the robot system of this embodiment, the master arm 2 is not provided, but the input device 7 is provided with a speed adjuster 73 which sends operational information for adjusting a speed of the slave arm 1 during operation along a scheduled route, to the motion controller 31. Here, the scheduled route is a planned route to be traced by the slave arm 1 while the slave arm 1 operates based on the automatic operational information. The speed adjuster 73 is configured to be operable, and may include, for example, a switch, an adjustment knob, a control lever, or a mobile terminal, such as a tablet computer. In this embodiment, the mode selector 71 is configured to be selectable by the operator, either one of the automatic mode and the correctable automatic mode as the operating mode in which the slave arm 1 is operated. In this embodiment, the speed adjuster 73 functions as the operation correcting device which corrects the operation of the slave arm 1 during operation.

One of the at least one saved operational information 61 stored in the storage device 6 is sent to the motion controller 31 as the automatic operational information for causing the slave arm 1 to automatically operate. Moreover, the manipulating information generated by manipulating the speed adjuster 73 is sent to the motion controller 31. In this embodiment, the saved operational information 61 and the manipulating information include the information related to a speed of the slave arm 1 along the scheduled route. Moreover, the saved operational information 61 also includes the route information related to the scheduled route of the slave arm 1.

The motion controller 31 uses one or both of the automatic operational information and the manipulating information according to the operating mode selected in the mode selector 71.

When the operating mode in which the slave arm 1 is operated is the automatic mode, the motion controller 31 controls the operation of the slave arm 1 using the automatic operational information sent from the storage device 6 according to the preset task program, without using the manipulating information sent from the speed adjuster 73. That is, the slave arm 1 moves along the scheduled route based on the speed information contained in the automatic operational information.

Moreover, when the operating mode in which the slave arm 1 is operated is the correctable automatic mode, the motion controller 31 controls the operation of the slave arm 1 using both the automatic operational information and the manipulating information in response to the reception of the manipulating information while the slave arm 1 is operating automatically using the automatic operational information. That is, the slave arm 1 moves along the scheduled route at a speed corrected from an operating speed based on the automatic operational information. Moreover, the storage device 6 stores the corrected operational information for the slave arm 1 moving along the scheduled route at the corrected speed, as the saved operational information 61. Thus, this embodiment also acquires the same effects as the first embodiment.

Other Embodiments

The present disclosure is not limited to the embodiments described above, and various modifications may be possible without departing from the spirit of the present disclosure.

For example, in the embodiments described above, although the route and/or the operating speed of the slave arm 1 are corrected by the operation correcting device of the present disclosure, the operation correcting device of the present disclosure may correct operation(s) other than the route and/or the operating speed of the slave arm 1. For example, the operation correcting device of the present disclosure may be a device which corrects one or more parameters related to operation(s) other than the route and/or the operating speed of the slave arm 1. For example, the operation correcting device of the present disclosure may send to the motion controller 31 manipulating information of the manipulation of the master arm 2 for adjusting an operating sensitivity of the slave arm 1, or may send to the motion controller 31 manipulating information for adjusting a feedback rate of a force received by the slave arm 1 to the master arm 2 side.

Moreover, the robot system of the present disclosure may be provided with a plurality of operation correcting devices. For example, it may be comprised of both the master arm 2 for correcting the route of the slave arm 1 and the speed adjuster 73 for adjusting the speed of the slave arm 1 along the route. In this case, for the location where the route needs to be corrected, the route of the slave arm 1 is correctable by the manipulation of the master arm 2, while lowering the speed by the speed adjuster 73. Thus, the route of the slave arm 1 is correctable with more accuracy.

In the embodiments described above, although the manipulating parts, such as the mode selector 71 and the operational information selector 72 are provided in the single input device 7, they may be provided in separate or different input devices.

DESCRIPTION OF REFERENCE CHARACTERS

1 Slave Arm (Robot Main Body)
2 Master Arm (Operation Correcting Device)
3 Control Device
31 Motion Controller
32 Saved Operational Information Generator
6 Storage Device (Memory Part)
61 Saved Operational Information
71 Mode Selector
72 Operational Information Selector
73 Speed Adjuster (Operation Correcting Device)
100 Robot System

What is claimed is:

1. A master-slave type robot system configured to allow an operator to manipulate a master arm while looking at a work situation of a slave arm to cause the slave arm to perform a specific work, comprising:
   the slave arm;
   a memory part configured to store information for causing the slave arm to perform a given operation, as saved operational information;
   a motion controller configured to control the operation of the slave arm by using the saved operational information as automatic operational information for causing the slave arm to operate; and the master arm installed outside a workspace of the slave arm and configured to be operated by the operator to generate manipulating information for correcting the operation of the slave arm during performance of the specific work, wherein the motion controller controls the slave arm to perform an operation corrected from the operation related to the automatic operational information in response to a reception of the manipulating information while the slave arm is operating by using the automatic operational information, and wherein the memory part is configured to store corrected operational information for causing the slave arm to perform the corrected operation as the saved operational information, when the slave arm performs the corrected operation.

2. The robot system of claim 1, wherein the motion controller controls the operation of the slave arm using the latest saved operational information stored in the memory part as the automatic operational information.

3. The robot system of claim 1,
wherein the memory part stores a plurality of saved operational information, and
wherein the robot system further comprises an operational information selector configured to select the saved operational information to be used as the automatic operational information, from the plurality of saved operational information stored in the memory part.

4. The robot system of claim 1,
wherein the memory part stores a plurality of saved operational information, and
wherein the robot system further comprises a saved operational information generator configured to generate new saved operational information using the plurality of saved operational information stored in the memory part.

5. The robot system of claim 1, further comprising:
a camera installed in a space where the slave arm is provided, the camera being configured to image the work situation of the slave arm; and
a monitor installed in a space where the master arm is provided, the monitor being configured to receive image information acquired by and sent from the camera and display the work situation of the slave arm.

* * * * *